United States Patent
Wenderow et al.

(10) Patent No.: US 8,694,157 B2
(45) Date of Patent: Apr. 8, 2014

(54) CATHETER CONTROL SYSTEM AND GRAPHICAL USER INTERFACE

(75) Inventors: Tal Wenderow, West Newton, MA (US); Thomas Bromander, Andover, MA (US); David Handler, Newton, MA (US)

(73) Assignee: Corindus, Inc., Waltham, MA (US)

( * ) Notice: Subject to any disclaimer, the term of this patent is extended or adjusted under 35 U.S.C. 154(b) by 152 days.

(21) Appl. No.: 13/034,630

(22) Filed: Feb. 24, 2011

(65) Prior Publication Data

US 2011/0152882 A1  Jun. 23, 2011

Related U.S. Application Data

(63) Continuation of application No. PCT/US2009/055320, filed on Aug. 28, 2009.

(60) Provisional application No. 61/093,242, filed on Aug. 29, 2008.

(51) Int. Cl.
*G06F 19/00* (2011.01)
*A61B 19/00* (2006.01)
*A61B 5/04* (2006.01)

(52) U.S. Cl.
USPC ............ 700/245; 606/130; 600/523; 600/525

(58) Field of Classification Search
None
See application file for complete search history.

(56) References Cited

U.S. PATENT DOCUMENTS

| | | |
|---|---|---|
| 2,718,598 A | 9/1955 | Graf |
| 3,147,953 A | 9/1964 | Arth |
| 3,308,297 A | 3/1967 | Mansker |
| 4,254,341 A | 3/1981 | Herr et al. |
| 4,382,184 A | 5/1983 | Wernikoff |
| 4,581,538 A | 4/1986 | Lenhart |
| 4,965,456 A | 10/1990 | Huettenrauch et al. |
| 4,977,588 A | 12/1990 | Van der Ende |
| 5,015,864 A | 5/1991 | Maleki |
| 5,049,147 A | 9/1991 | Danon |

(Continued)

FOREIGN PATENT DOCUMENTS

| | | |
|---|---|---|
| DE | 2856439 A | 7/1980 |
| DE | 4233323 A | 4/1994 |

(Continued)

OTHER PUBLICATIONS

Beyar et al., Remote-Control Percutaneous Coronary Interventions: Concept, Validation, and First-in-Humans Pilot Clinical Trial, Journal of the American College of Cardiology, Sep. 24, 2005, 5 pages.

(Continued)

*Primary Examiner* — Khoi Tran
*Assistant Examiner* — Robert Nguyen
(74) *Attorney, Agent, or Firm* — Rathe Lindenbaum LLP

(57) ABSTRACT

A remote workstation for the control of percutaneous intervention devices is provided. The remote workstation includes a control system for remotely and independently controlling at least two percutaneous intervention devices. The control system includes at least one input device to control the percutaneous intervention devices. The control system controls movement of at least one of the percutaneous intervention devices along at least two degrees of freedom. The remote workstation also includes a graphical user interface for displaying icons representative of the operational status of each of the percutaneous intervention devices.

11 Claims, 9 Drawing Sheets

(56) References Cited

U.S. PATENT DOCUMENTS

| | | | |
|---|---|---|---|
| 5,090,044 A | 2/1992 | Kobayashi | |
| 5,133,364 A | 7/1992 | Palermo et al. | |
| 5,139,473 A | 8/1992 | Bradshaw et al. | |
| 5,185,778 A | 2/1993 | Magram | |
| 5,217,474 A | 6/1993 | Zacca et al. | |
| 5,318,541 A | 6/1994 | Viera et al. | |
| 5,351,676 A | 10/1994 | Putman | |
| 5,377,678 A | 1/1995 | Dumoulin et al. | |
| 5,396,880 A | 3/1995 | Kagan et al. | |
| 5,423,321 A | 6/1995 | Fontenot | |
| 5,425,382 A | 6/1995 | Golden et al. | |
| 5,434,775 A * | 7/1995 | Sims et al. | 705/7.12 |
| 5,464,023 A | 11/1995 | Viera | |
| 5,484,407 A | 1/1996 | Osypka | |
| 5,487,734 A | 1/1996 | Thorne et al. | |
| 5,492,131 A | 2/1996 | Galel | |
| 5,524,180 A | 6/1996 | Wang et al. | |
| 5,540,649 A | 7/1996 | Bonnell et al. | |
| 5,578,014 A | 11/1996 | Erez et al. | |
| 5,584,078 A | 12/1996 | Saboory | |
| 5,586,968 A | 12/1996 | Grundl et al. | |
| 5,623,943 A | 4/1997 | Hackett et al. | |
| 5,644,613 A | 7/1997 | Mick | |
| 5,654,864 A | 8/1997 | Ritter et al. | |
| 5,690,645 A | 11/1997 | Van Erp | |
| 5,697,377 A | 12/1997 | Wittkampf | |
| 5,704,897 A | 1/1998 | Truppe | |
| 5,706,827 A | 1/1998 | Ehr et al. | |
| 5,728,044 A | 3/1998 | Shan | |
| 5,741,271 A | 4/1998 | Nakao et al. | |
| 5,779,623 A | 7/1998 | Bonnell | |
| 5,821,920 A | 10/1998 | Rosenberg et al. | |
| 5,842,987 A | 12/1998 | Sahadevan | |
| 5,851,182 A | 12/1998 | Sahadevan | |
| 5,860,923 A * | 1/1999 | Lenker et al. | 600/433 |
| 5,882,333 A | 3/1999 | Schaer et al. | |
| 5,957,941 A | 9/1999 | Ream | |
| 5,981,964 A | 11/1999 | McAuley et al. | |
| 6,004,276 A | 12/1999 | Wright et al. | |
| 6,013,038 A | 1/2000 | Pflueger | |
| 6,024,749 A | 2/2000 | Shturman et al. | |
| 6,048,300 A | 4/2000 | Thornton et al. | |
| 6,078,832 A * | 6/2000 | Lenker et al. | 600/433 |
| 6,083,170 A | 7/2000 | Ben-Haim | |
| 6,096,004 A | 8/2000 | Meglan et al. | |
| 6,126,647 A | 10/2000 | Posey et al. | |
| 6,171,234 B1 | 1/2001 | White et al. | |
| 6,233,476 B1 | 5/2001 | Strommer et al. | |
| 6,258,052 B1 | 7/2001 | Milo | |
| 6,261,247 B1 | 7/2001 | Ishikawa et al. | |
| 6,266,552 B1 | 7/2001 | Slettenmark | |
| 6,285,898 B1 | 9/2001 | Ben-Haim | |
| 6,290,675 B1 | 9/2001 | Vujanic et al. | |
| 6,351,513 B1 | 2/2002 | Bani-Hashemi et al. | |
| 6,358,199 B1 | 3/2002 | Pauker et al. | |
| 6,375,471 B1 | 4/2002 | Wendlandt et al. | |
| 6,447,504 B1 | 9/2002 | Ben-Haim et al. | |
| 6,448,571 B1 | 9/2002 | Goldstein | |
| 6,497,444 B1 | 12/2002 | Simon | |
| 6,499,163 B1 | 12/2002 | Stensby | |
| 6,522,909 B1 | 2/2003 | Garibaldi et al. | |
| 6,540,670 B1 | 4/2003 | Hirata et al. | |
| 6,554,472 B1 | 4/2003 | Dietz et al. | |
| 6,610,007 B2 | 8/2003 | Belson et al. | |
| 6,653,648 B2 | 11/2003 | Goldstein | |
| 6,705,990 B1 * | 3/2004 | Gallant et al. | 600/300 |
| 6,726,675 B1 * | 4/2004 | Beyar | 604/510 |
| 6,740,103 B2 | 5/2004 | Hall et al. | |
| 6,770,066 B2 | 8/2004 | Weaver et al. | |
| 6,835,173 B2 | 12/2004 | Couvillon, Jr. | |
| 6,878,106 B1 | 4/2005 | Herrmann | |
| 6,997,870 B2 | 2/2006 | Couvillon, Jr. | |
| 7,087,013 B2 | 8/2006 | Belson et al. | |
| 7,112,811 B2 | 9/2006 | Lemer | |
| 7,276,044 B2 | 10/2007 | Ferry et al. | |
| 7,294,135 B2 | 11/2007 | Stephens et al. | |
| 7,608,847 B2 | 10/2009 | Rees | |
| 7,615,032 B2 | 11/2009 | Whittaker et al. | |
| 7,615,042 B2 | 11/2009 | Beyar et al. | |
| 7,632,265 B2 | 12/2009 | Hauck et al. | |
| 7,663,128 B2 | 2/2010 | Arterson | |
| 7,666,135 B2 | 2/2010 | Couvillon, Jr. | |
| 7,686,816 B2 | 3/2010 | Belef et al. | |
| 7,697,972 B2 | 4/2010 | Verard et al. | |
| 7,706,894 B2 | 4/2010 | Stewart et al. | |
| 7,729,743 B2 | 6/2010 | Sabczynski et al. | |
| 7,766,894 B2 | 8/2010 | Weitzner et al. | |
| 7,769,427 B2 | 8/2010 | Shachar | |
| D626,250 S | 10/2010 | Wenderow et al. | |
| 7,811,294 B2 | 10/2010 | Strommer et al. | |
| 7,848,788 B2 | 12/2010 | Tulley et al. | |
| 7,887,549 B2 | 2/2011 | Wenderow et al. | |
| 7,905,853 B2 | 3/2011 | Chapman et al. | |
| 7,967,773 B2 | 6/2011 | Amborn et al. | |
| 7,984,659 B2 | 7/2011 | Fujimoto et al. | |
| 8,043,362 B2 | 10/2011 | Gong et al. | |
| 8,046,049 B2 | 10/2011 | Govari et al. | |
| 8,187,229 B2 | 5/2012 | Weitzner et al. | |
| 8,257,302 B2 | 9/2012 | Beyar et al. | |
| 8,343,096 B2 | 1/2013 | Kirschenman et al. | |
| 8,390,438 B2 * | 3/2013 | Olson et al. | 340/407.1 |
| 2001/0025142 A1 | 9/2001 | Wessels et al. | |
| 2002/0042582 A1 * | 4/2002 | Vrba et al. | 600/585 |
| 2002/0087166 A1 | 7/2002 | Brock et al. | |
| 2002/0109107 A1 | 8/2002 | Goldstein | |
| 2002/0115931 A1 | 8/2002 | Strauss et al. | |
| 2002/0168618 A1 | 11/2002 | Anderson et al. | |
| 2002/0177789 A1 | 11/2002 | Ferry et al. | |
| 2003/0036712 A1 | 2/2003 | Heh et al. | |
| 2003/0040671 A1 | 2/2003 | Somogyi et al. | |
| 2003/0069719 A1 | 4/2003 | Cunningham et al. | |
| 2003/0078003 A1 | 4/2003 | Hunter et al. | |
| 2003/0088209 A1 | 5/2003 | Chiu et al. | |
| 2003/0176770 A1 | 9/2003 | Merril et al. | |
| 2003/0199848 A1 | 10/2003 | Ledesma et al. | |
| 2003/0210259 A1 | 11/2003 | Liu et al. | |
| 2004/0015974 A1 | 1/2004 | Jeyaraman | |
| 2004/0044279 A1 | 3/2004 | Lewin et al. | |
| 2004/0064086 A1 | 4/2004 | Gottlieb et al. | |
| 2004/0068173 A1 | 4/2004 | Viswanathan | |
| 2004/0085294 A1 | 5/2004 | Michelitsch et al. | |
| 2004/0113498 A1 | 6/2004 | Kroenke | |
| 2004/0138548 A1 | 7/2004 | Strommer et al. | |
| 2004/0152974 A1 | 8/2004 | Solomon | |
| 2004/0254566 A1 | 12/2004 | Plicchi et al. | |
| 2005/0008210 A1 | 1/2005 | Evron et al. | |
| 2005/0107697 A1 * | 5/2005 | Berke | 600/431 |
| 2005/0119615 A1 | 6/2005 | Noriega et al. | |
| 2005/0203382 A1 | 9/2005 | Govari et al. | |
| 2005/0203394 A1 * | 9/2005 | Hauck | 600/437 |
| 2005/0222554 A1 | 10/2005 | Wallace et al. | |
| 2005/0245846 A1 | 11/2005 | Casey | |
| 2005/0256504 A1 | 11/2005 | Long et al. | |
| 2005/0273199 A1 * | 12/2005 | Ban et al. | 700/248 |
| 2005/0277851 A1 | 12/2005 | Whittaker et al. | |
| 2005/0283075 A1 * | 12/2005 | Ma et al. | 600/441 |
| 2006/0041181 A1 | 2/2006 | Viswanathan et al. | |
| 2006/0041245 A1 | 2/2006 | Ferry et al. | |
| 2006/0066574 A1 | 3/2006 | Kim et al. | |
| 2006/0074442 A1 | 4/2006 | Noriega et al. | |
| 2006/0084911 A1 | 4/2006 | Belef et al. | |
| 2006/0116575 A1 | 6/2006 | Willis | |
| 2006/0146010 A1 | 7/2006 | Schneider | |
| 2006/0229587 A1 | 10/2006 | Beyar et al. | |
| 2006/0258935 A1 | 11/2006 | Pile-Spellman et al. | |
| 2006/0282140 A1 | 12/2006 | Schock et al. | |
| 2007/0016029 A1 | 1/2007 | Donaldson et al. | |
| 2007/0043338 A1 | 2/2007 | Moll et al. | |
| 2007/0060879 A1 | 3/2007 | Weitzner et al. | |
| 2007/0083193 A1 | 4/2007 | Werneth et al. | |
| 2007/0103437 A1 | 5/2007 | Rosenberg | |
| 2007/0106247 A1 | 5/2007 | Burnett et al. | |
| 2007/0118079 A1 | 5/2007 | Moberg et al. | |
| 2007/0123070 A1 | 5/2007 | Bencteux | |

(56) References Cited

U.S. PATENT DOCUMENTS

| | | | |
|---|---|---|---|
| 2007/0142749 A1 | 6/2007 | Khatib et al. | |
| 2007/0167801 A1* | 7/2007 | Webler et al. | 600/459 |
| 2007/0185480 A1* | 8/2007 | El-Galley et al. | 606/34 |
| 2007/0185486 A1 | 8/2007 | Hauck et al. | |
| 2007/0197896 A1 | 8/2007 | Moll et al. | |
| 2007/0239106 A1 | 10/2007 | Weitzner et al. | |
| 2007/0250097 A1 | 10/2007 | Weitzner et al. | |
| 2007/0276216 A1 | 11/2007 | Beyar et al. | |
| 2007/0276234 A1 | 11/2007 | Shahidi | |
| 2008/0027313 A1 | 1/2008 | Shachar | |
| 2008/0051820 A1 | 2/2008 | Gong et al. | |
| 2008/0059598 A1 | 3/2008 | Garibaldi et al. | |
| 2008/0097224 A1 | 4/2008 | Murphy et al. | |
| 2008/0146922 A1* | 6/2008 | Steins et al. | 600/437 |
| 2008/0146954 A1* | 6/2008 | Bojovic et al. | 600/512 |
| 2008/0161801 A1 | 7/2008 | Steinke et al. | |
| 2008/0167750 A1* | 7/2008 | Stahler et al. | 700/245 |
| 2008/0217564 A1 | 9/2008 | Beyar et al. | |
| 2008/0221922 A1* | 9/2008 | Putnam et al. | 705/2 |
| 2008/0221992 A1 | 9/2008 | Bernstein | |
| 2008/0229597 A1* | 9/2008 | Malandain | 33/512 |
| 2008/0249536 A1* | 10/2008 | Stahler et al. | 606/130 |
| 2008/0319275 A1* | 12/2008 | Chiu et al. | 600/300 |
| 2009/0012533 A1 | 1/2009 | Barbagli et al. | |
| 2009/0105639 A1 | 4/2009 | Weitzner et al. | |
| 2009/0110152 A1 | 4/2009 | Manzke et al. | |
| 2009/0124915 A1* | 5/2009 | MacAdam | 600/523 |
| 2009/0131955 A1 | 5/2009 | Wenderow et al. | |
| 2009/0137952 A1 | 5/2009 | Ramamurthy et al. | |
| 2009/0138025 A1 | 5/2009 | Stahler et al. | |
| 2009/0221958 A1 | 9/2009 | Beyar et al. | |
| 2009/0247944 A1 | 10/2009 | Kirschenman et al. | |
| 2010/0056958 A1* | 3/2010 | Ravi | 600/587 |
| 2010/0063630 A1* | 3/2010 | Sutherland et al. | 700/264 |
| 2010/0069833 A1 | 3/2010 | Wenderow et al. | |
| 2010/0073150 A1* | 3/2010 | Olson et al. | 340/407.1 |
| 2010/0076308 A1 | 3/2010 | Wenderow et al. | |
| 2010/0076309 A1 | 3/2010 | Wenderow et al. | |
| 2010/0076310 A1 | 3/2010 | Wenderow et al. | |
| 2010/0084586 A1 | 4/2010 | Teodorescu | |
| 2010/0130987 A1 | 5/2010 | Wenderow et al. | |
| 2010/0175701 A1 | 7/2010 | Reis et al. | |
| 2011/0015569 A1* | 1/2011 | Kirschenman et al. | 604/95.01 |
| 2011/0109283 A1 | 5/2011 | Kapels et al. | |
| 2011/0144658 A1 | 6/2011 | Wenderow et al. | |
| 2011/0152882 A1 | 6/2011 | Wenderow et al. | |
| 2012/0179032 A1 | 7/2012 | Bromander et al. | |

FOREIGN PATENT DOCUMENTS

| | | |
|---|---|---|
| EP | 0 329 492 A2 | 8/1989 |
| EP | 0 331 944 A1 | 9/1989 |
| EP | 0 554 986 B1 | 1/1993 |
| EP | 0 590 268 B1 | 4/1994 |
| EP | 0 970 663 A1 | 1/2000 |
| EP | 1 415 660 A1 | 5/2004 |
| EP | 1 442 720 A1 | 8/2004 |
| EP | 1554986 A | 7/2005 |
| EP | 1792638 A | 6/2007 |
| EP | 1 504 713 B1 | 7/2008 |
| FR | 2167098 A | 8/1973 |
| JP | 07184923 | 7/1995 |
| JP | 7328016 | 12/1995 |
| SU | 279814 A | 7/1975 |
| SU | 992067 A | 1/1983 |
| WO | 9320876 A | 10/1993 |
| WO | 9502233 A | 1/1995 |
| WO | 9621486 A | 7/1996 |
| WO | WO 01/74252 A2 | 10/2001 |
| WO | 0209571 A | 2/2002 |
| WO | WO 02/09571 A2 | 2/2002 |
| WO | 02064011 A | 8/2002 |
| WO | 2005000105 A | 1/2005 |
| WO | 2006018841 A | 2/2006 |
| WO | WO 2006/120666 A1 | 11/2006 |
| WO | 2007036925 A | 4/2007 |
| WO | WO 2009/137410 A1 | 11/2009 |
| WO | WO 2010/025336 A1 | 3/2010 |
| WO | WO 2010/025338 A1 | 3/2010 |
| WO | WO 2010/068783 A1 | 6/2010 |
| WO | WO 2010/107916 A1 | 9/2010 |
| WO | WO 2011/046874 A1 | 4/2011 |

OTHER PUBLICATIONS

U.S. Appl. No. 29/378,948, filed Nov. 11, 2010, Murphy.

Anderson, J., Chui, C.K., Cai. Y., Wang Y., Eng, Z.L.M., Eng, X.M. M., Nowinski, W., Solaiyappan, M., Murphy, K, Gailloud, P. & Venbrux, A., Virtual Reality Training in International Radiology: The John Hopkins and Kent Ridge Digital Labratory Experience, Theime Medical Publishers, 2002, 2 pages, vol. 19, No. 2, New York, NY.

Becker, Y, Cancer in ataxia-telangiectasia patients: Analysis of factors leading to radiation-induced and spontaneous tumors, Anticancer Res., 1986, vol. 6, No. 5, Abstract, pp. 1021-1032, Israel.

Biazzi, L. & Garbagna, P., Exposition Aux Radiations Et Protection Pendant Les Examens Angiographiques, Ann. Radiol., 1979, vol. 22, No. 4, Abstract, pp. 345-347, France.

Essinger A., Raimondi, S. & Valley, J.F., Radiation Exposure to the Examiner During Coronary Angiography, Ann. Radiol., 1979 vol. 22 No. 4 Abstract, pp. 340-343, France.

Favaretti, C., Stritoni, P., Mariotti, A., Bressan, M. & Razzolini, R., The Distribution and Activities of Hemodynamic Laboratories in Italy: The implications for the Quality of Services, G Ital Cardiol, May 1994, vol. 24 No. 5, Abstract, pp. 477-482, Italy.

Magnavita, N. & Fileni, A., Occupational risk caused by ultrasound in medicine, Radiologica Medica, Jul.-Aug. 1994 vol. 88, No. 1-2, Abstract, pp. 107-111, Italy.

Roach, H., Larson, E., Cobran, T. & Bartlett, B., Intravenous site care practices in critical care: a national survey, Heart Lung, Sep.-Oct. 1995 vol. 24, No. 5, Abstract, pp. 420-424, Washington D.C., United States.

Van Den Brand, M., Utilization or coronary angioplasty and cost or angioplasty disposables in 14 western European countries, Europe Heart Journal, Mar. 1993 vol. 14, No. 3, Abstract, pp. 391-397, Rotterdam, Netherlands.

Wu, J.R., Huang, T.Y., Wu, D.K., Hsu, P.C. & Weng, P.S., An investigation of radiation exposure on pediatric patients and doctors during cardiac catheterization and cineangiography, Journal of Medical Sciences, Sep. 1991, vol. 7, No. 9, Abstract, pp, 448-453, Taiwan, China.

Machine Translation of DE 4,23,323.

Machine Translation of FR 2,167,098.

Machine Translation of JP 7,184,923.

Machine Translation of JP 7,328,016.

Barker Brettell, Response to Communication Pursuant to Article 94 (3) EPC for Application No. 09810642.0, Aug. 9, 2012, 2 pages.

European Patent Office, Communication Pursuant to Article 94 (3) EPC for Application No. 09810642.0, Jun. 8, 2012, 7 pages.

European Patent Office, Communication Pursuant to Article 94 (3) EPC for Application No. 09810642.0, Nov. 29, 2012, 4 pages.

\* cited by examiner

CATHETER CONTROL SYSTEM AND GRAPHICAL USER INTERFACE

CROSS-REFERENCE TO RELATED PATENT APPLICATIONS

This application is a continuation of prior international Application No. PCT/US09/055320, filed Aug. 28, 2009, which claims the benefit of U.S. Provisional Application No. 61/093,242, filed Aug. 29, 2008, both of which are incorporated herein by reference in their entireties.

BACKGROUND OF THE INVENTION

The present invention relates generally to the field of catheter systems for performing diagnostic and/or therapeutic procedures. The present invention relates specifically to catheter systems including a user interface and/or workstation for controlling a robotic catheter system.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based therapeutic procedure, such as angioplasty. Catheter based therapeutic procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based therapeutic procedure. During one type of therapeutic procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other disease may be treated with catheterization procedures.

SUMMARY OF THE INVENTION

One embodiment of the invention relates to a remote workstation for the control of percutaneous intervention devices. The remote workstation includes a control system for remotely and independently controlling at least two percutaneous intervention devices. The control system includes at least one input device to control the percutaneous intervention devices. The control system controls movement of at least one of the percutaneous intervention devices along at least two degrees of freedom. The remote workstation also includes a graphical user interface for displaying icons representative of the operational status of each of the percutaneous intervention devices.

Another embodiment of the invention relates to a remote workstation for the control of percutaneous intervention devices to perform a catheter based medical procedure on a patient, the remote workstation. The remote workstation includes at least one input device operatively coupled to the control system and a control system for remotely and independently controlling at least two percutaneous intervention devices. The control system receives at least one user input from the at least one input device to control the percutaneous intervention devices, and the control system controls movement of the percutaneous intervention devices along at least two degrees of freedom. The remote workstation also includes a graphical user interface for displaying a first set of icons and a second set of icons. The first set of icons is representative of each of the percutaneous intervention devices, and the second set of icons is representative of physiological information of the patient.

Another embodiment of the invention relates to a remote workstation for the control of percutaneous intervention devices located within a first lab unit. The remote workstation includes a first input device and a second input device. The remote workstation also includes a control system for remotely controlling a first percutaneous intervention device and a second percutaneous intervention device. The first and second input devices are operatively coupled to the control system, and the control system controls movement of the first and second percutaneous intervention devices along at least two degrees of freedom in response to user input signals received from the first and second input devices. The remote workstation also includes a graphical user interface for displaying a first icon representative of the operational status of the first percutaneous intervention device and a second icon representative of the operational status the second percutaneous intervention device.

Another embodiment of the invention relates to a method for measuring the length of a structure during a percutaneous procedure. The method includes aligning a portion of a percutaneous device with a first end of the structure and moving the percutaneous device so that the portion of the percutaneous device moves from the first end of the structure to a second end of the structure. The method also includes aligning the portion of the percutaneous device with the second end of the structure, measuring the distance moved by the percutaneous device to move the portion of the percutaneous device between the first end and the second end of the structure, and providing information to the user regarding the measured distanced.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
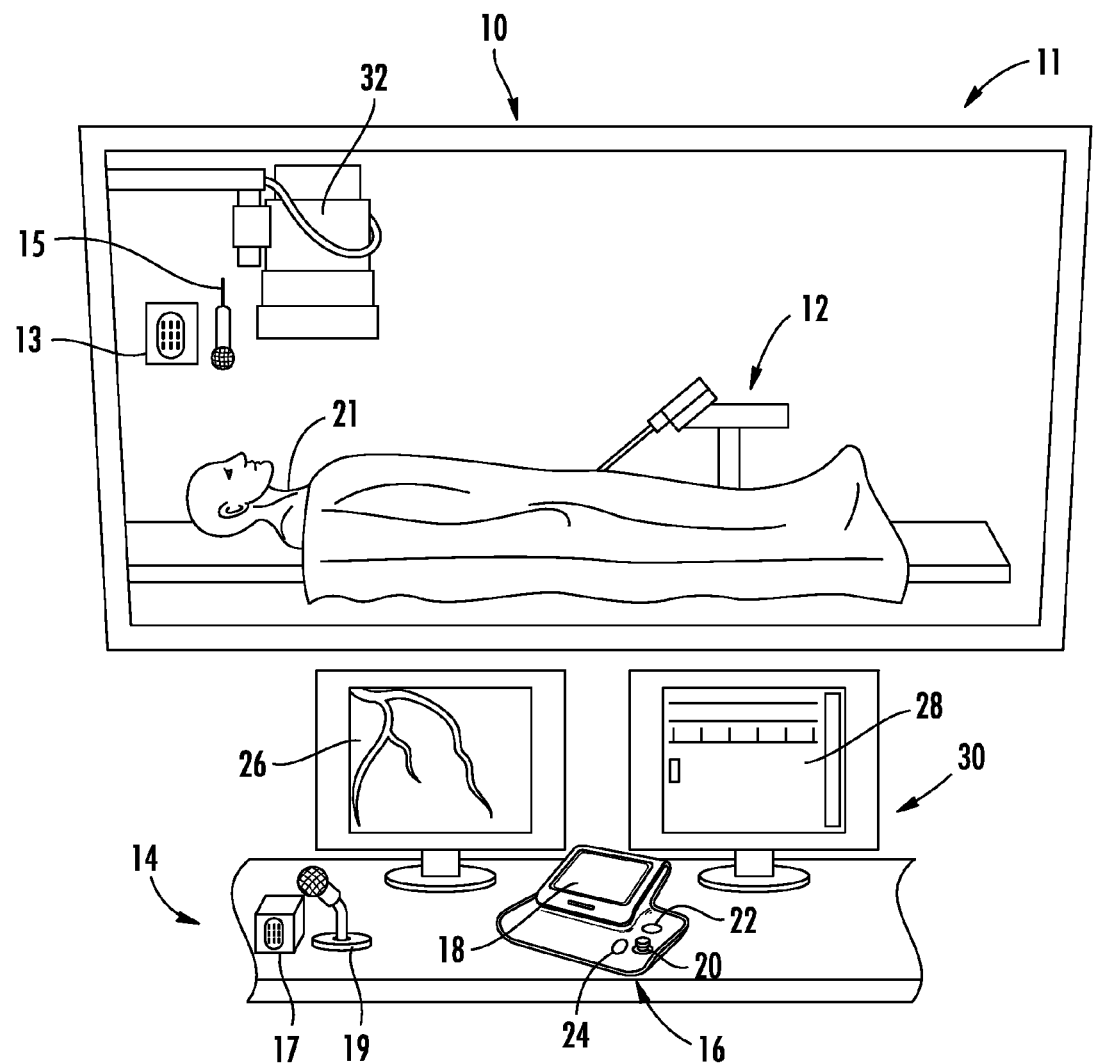
FIG. 1 is a perspective view of the robotic catheter system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous intervention devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous intervention devices or components (e.g., guide wires, guide catheters, working catheters, catheter balloons, stents, contrast media, medicine, diagnostic catheters, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in U.S. Provisional Application No. 61/050,933, filed May 6, 2008, which is incorporated herein by reference in its entirety. Other embodiments of bedside system 12 are described in detail in International Application No. PCT/US2009/042720, filed May 4, 2009, which is incorporated herein by reference in its entirety.

In one embodiment, bedside system 12 may be equipped to perform a catheter based diagnostic procedure. In this embodiment, bedside system 12 may be equipped with a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In this embodiment, bedside system 12 may be equipped with a guide catheter, a guide wire, and a working catheter (e.g., a balloon catheter, a stent delivery catheter, etc.). In another embodiment, bedside system 12 may be equipped with an intravascular ultrasound (IVUS) catheter. In another embodiment, any of the percutaneous intervention devices of bedside system 12 may be equipped with positional sensors that indicate the position of the component within the body.

Bedside system 12 is in communication with workstation 14, allowing signals generated by the user inputs of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30. User interface 30 includes controls 16. Controls 16 allow the user to control bedside system 12 to perform a catheter based medical procedure. Controls 16 may be configured to control movement of the percutaneous intervention devices along at least two degrees of freedom. For example, controls 16 may be configured to cause bedside system 12 to perform various tasks using the various percutaneous intervention devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure).

Figure 4:
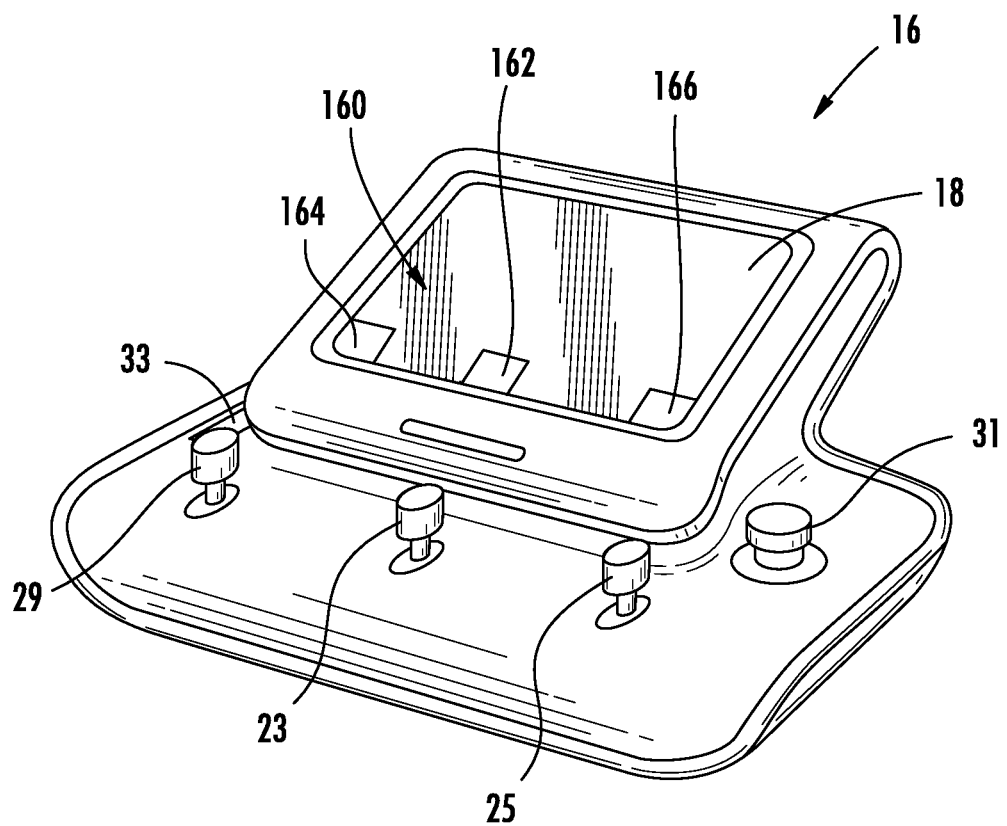
FIG. 4 is perspective view of controls for a robotic catheter system according to an exemplary embodiment.

In one embodiment, workstation 14 includes a single set of controls 16 that are configured to control all of the percutaneous intervention devices (e.g., guide wires, catheters, catheter balloons, stents, diagnostic catheters, contrast medium, medicine, etc.) that may be used with bedside system 12. In this embodiment, controls 16 will include a switch or toggle that allows the user to select which task bedside system 12 will currently perform. In another embodiment, controls 16 may include one or more dedicated sets of controls configured to control bedside system 12 only during the performance of a particular task. For example, as shown in FIG. 4, workstation 14 may include a guide wire control 23, a working catheter control 25, and a guide catheter control 29. In this embodiment, guide wire control 23 is configured to advance, retract, or rotate a guide wire, working catheter control 25 is configured to advance, retract, or rotate a working catheter, and guide catheter control 29 is configured to advance, refract, or rotate a guide catheter. Controls 16 may also include a balloon control that is configured to inflate or deflate a balloon and/or a stent. Each of the dedicated controls may include one or more buttons, joysticks, touch screens, etc. that may be desirable to control the particular component to which the control is dedicated. In one embodiment, controls 16 are configured to allow the user to operate more than one component via bedside system 12 at the same time. For example, in this embodiment, the user may operate guide wire control 23, working catheter control 25, and/or guide catheter control 29 at the same time to advance, refract, and/or rotate a guide wire, a working catheter, and/or a guide catheter at the same time.

In an exemplary embodiment of FIG. 1, controls 16 include a touch screen 18, a pair of joysticks 20 having variable speed control, a first jog button 22 for 1 mm jogs, and a second jog button 24 for 5 mm jogs. First jog button 22 and second jog button 24 have continuous jog capability. Operation of jog buttons 22 and 24 may be configured to cause bedside system 12 to move a guide wire or a catheter. In one embodiment, depression of one or more of the jog buttons will move a guide wire or catheter a set distance forward as noted above. However, jog buttons 22 and 24 may be configured to move a guide wire or a catheter any distance that may be desired. In one embodiment, controls 16 may be configured to allow the user to set the distance that a component moves in response to operation of jog buttons 22 and 24 (e.g., 2 mm jogs, 3 mm jogs, 4 mm jogs, 6 mm jogs, 7 mm jogs, etc.). The user may set the distance that a component moves in response to operation of jog buttons 22 and 24 via a separate control, such as a dial, entry of the desired distance via a keyboard or touch screen, entry of the desired distance via selection of desired distance from a menu displayed on one of the displays of workstation 14, etc. In addition, controls 16 may include a rotational jog button configured to rotate a guide wire or a catheter a pre-set number of degrees when pressed. Another button may be used to accelerate the speed of a guide wire or a catheter or to provide a multiplier so that the variable speed control reacts in a heightened manner. For example, if movement of a joystick a set distance results in the movement of the guide wire at a set speed in normal operation, the guide wire would move at a multiple of the set speed by depressing the button to accelerate the speed. In another embodiment, the various controls (e.g., jog buttons 22 and 24, joysticks 20, etc.) may be graphic touch screen controls.

Referring to FIG. 4, an exemplary embodiment of controls 16 is shown. In this embodiment, controls 16 includes a touch screen 18, a guide catheter control 29, a guide wire control 23, and a working catheter control 25. In this embodiment, guide catheter control 29, guide wire control 23, and working catheter control 25 are joysticks that allow the user to advance, refract, and rotate the component associated with the control. As shown in FIG. 4, in an exemplary embodiment, guide catheter control 29 is positioned on the far left, guide wire control 23 is positioned in the middle, and working catheter control 25 is positioned to the far right below touch screen 18. In another embodiment, each of the joysticks shown in FIG. 4 may be assigned to control a particular component based upon the preference of the user. For example, the left most joystick shown may be assigned to control the working catheter and the right most joystick may be assigned to control the guide catheter. In another embodiment, one or more portions of controls 16 are configured to provide haptic feedback (i.e., feedback through sense of touch) to the user. For example, the joysticks of controls 23, 25, and 29 may vibrate when the user is advancing the associated component or may apply a force to indicate resistance experienced by the associated component as the user attempts to move the component via manipulation of the control.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

In the embodiment shown in FIG. 4, the controls 23, 25, and 29 are shown equally spaced from each other aligned beneath touch screen 18. In other embodiments, controls 23, 25, and 29 are not aligned beneath touch screen 18 but are staggered. In another embodiment, the space between working catheter control 25 and guide wire control 23 is greater than the distance between guide wire control 23 and guide catheter control 29. Controls 16 may include one or more ergonomic hand supports to support the user's hand while operating controls 16. In another embodiment, controls 16 may include a keyboard and/or a mouse. The keyboard and/or mouse may be separate input devices coupled via a communication link 38 to controller 40, and/or the keyboard and/or mouse may be integrated with one or more components of workstation 14.

In one embodiment, workstation 14 and/or controls 16 include one or more devices and/or systems to control access to and/or use of various component. For example, controls 16 may be password protected, may include a fingerprint reader, a badge reader, etc. In these embodiments, controls 16 may not operate bedside system 12 unless a correct password is entered, an authorized finger print or badge is read, etc.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 26 and second monitor 28 may be configured to display procedure specific information (e.g., duration of procedure, catheter or guide wire position, volume of medicine or contrast agent delivered, etc.). In one embodiment, first monitor 26 is configured to display a real-time image of a patient's heart during a catheterization procedure, and second monitor 28 is configured to display graphical user interface 160 as discussed below. In another embodiment, user interface 30 includes a third monitor configured to display hemodynamic data. In another embodiment, user interface 30 includes a single screen of sufficient size to display one or more of the displays and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device including a C-arm that allows imaging system 32 to partially or completely rotate around patient 21 in order to obtain images at different angular positions relative to the patient (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, catheter, stent, etc. during the procedure. The image or images may be displayed on first monitor 26 and/or second monitor 28. In addition, controls 16 may also be configured to allow the user positioned at workstation 14 to control various functions of imaging system 32 (e.g., image capture, magnification, collimation, c-arm positioning, etc.).

Workstation 14 is capable of being remotely located, for example, in either a procedure room or a separate control room. Workstation 14 may be located at any place within a hospital. Workstation 14 may also be in at any location outside of the hospital, such as in a physician's offsite office, mobile workstation trailer, etc. If workstation 14 is located such that the user is not able to directly view patient 21 within lab unit 11, lab unit 11 may be equipped with a camera to allow the user located at workstation 14 to see the patient within lab unit 11. If imaging system 32 is a radiation based imaging device, remotely locating workstation 14 enables users to perform procedures outside the radiation zone created by imaging system 32. This may eliminate the need to wear heavy lead garments. This reduces orthopedic occupational hazards, including, but not limited to, spinal injuries and general strain on the body of the operator. A second benefit of remotely locating workstation 14 is that the dangers associated with radiation exposure are reduced. A third benefit of remotely locating workstation 14 is that it allows users to multitask outside the procedure room during downtime.

Figure 6:
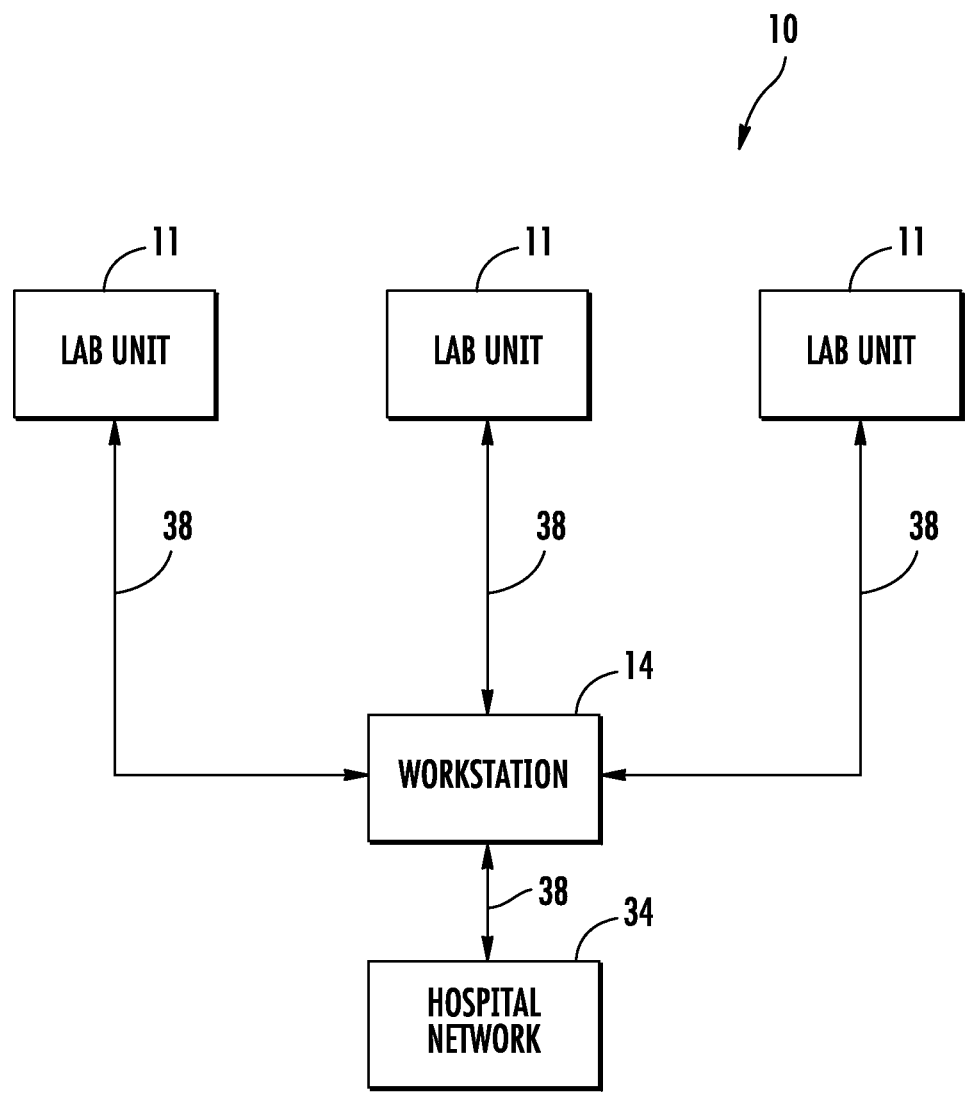
FIG. 6 is a diagram of a robotic catheter system including multiple lab units according to an exemplary embodiment.

In an exemplary embodiment shown in FIG. 6, a single workstation 14 may be in communication with multiple lab units 11. Each lab unit 11 may be equipped as discussed above regarding FIGS. 1 and 2. The single workstation 14 may be configured to operate a bedside system, an imaging system, and/or a communication system that are located within each of the lab units. In this embodiment, controls 16 may include a switch or other suitable selection device that allows the user located at workstation 14 to select which lab unit 11 workstation 14 is currently controlling. This configuration may increase the productivity and efficiency of workstation 14. For instance, this configuration may allow the user positioned at workstation 14 to perform a catheter based medical procedure on a first patient using a first bedside system located in the first lab unit while another patient is being prepared (e.g., anesthetized, connected to monitoring devices, etc.) for a procedure to be preformed in the second lab unit. In one embodiment, the single workstation 14 may be located at a different site than one or more of the lab units that it is controlling. In this embodiment, each lab unit 11 may be equipped with a camera to allow the user located at workstation 14 to see each of the patients within each lab unit 11. In another embodiment, multiple workstations 14 may control a single lab unit 11. In one embodiment, there is a master-slave relationship between the multiple workstations.

Referring to FIG. 1, catheter procedure system 10 may include a communication system that allows the user positioned at workstation 14 to communicate with patient 21 positioned within lab unit 11. The communication system, may include a first voice output unit, shown as lab unit speaker 13, a first voice input unit, shown as lab unit microphone 15, a second voice output unit, shown as workstation speaker 17, and a second voice input unit, shown as workstation microphone 19. Workstation microphone 19 is configured to transmit the voice of the user of workstation 14 to lab unit speaker 13. Lab unit microphone 15 is configured to transmit the voice of patient 21 to workstation speaker 17. The communication system may include one or more switches (e.g., on/off switch, mute switch, etc.) to turn off workstation microphone 19 and/or lab unit microphone 15. Speaker 13 and/or speaker 17 may also include on/off switches and/or volume control switches. In one embodiment, controller 40 is configured to operate the communication system.

In one embodiment, lab unit speaker 13 and/or workstation speaker 17 may be a set of headphones or earphones that patient 21 and/or the user of workstation 14, respectively, may wear. In another embodiment, lab unit speaker 13, lab unit microphone 15, workstation speaker 17, and workstation microphone 19 comprise a wireless remote communication system. In this embodiment, workstation speaker 17 and workstation microphone 19 may be part of a wireless headset that the user of workstation 14 can wear while performing a catheter based procedure. Use of a wireless headset may allow the user to move more freely about workstation 14 and remain in communication with patient 21 and it may also eliminate problems that may associated with cords under certain circumstances (e.g., tangling, tripping, etc.).

Figure 2:
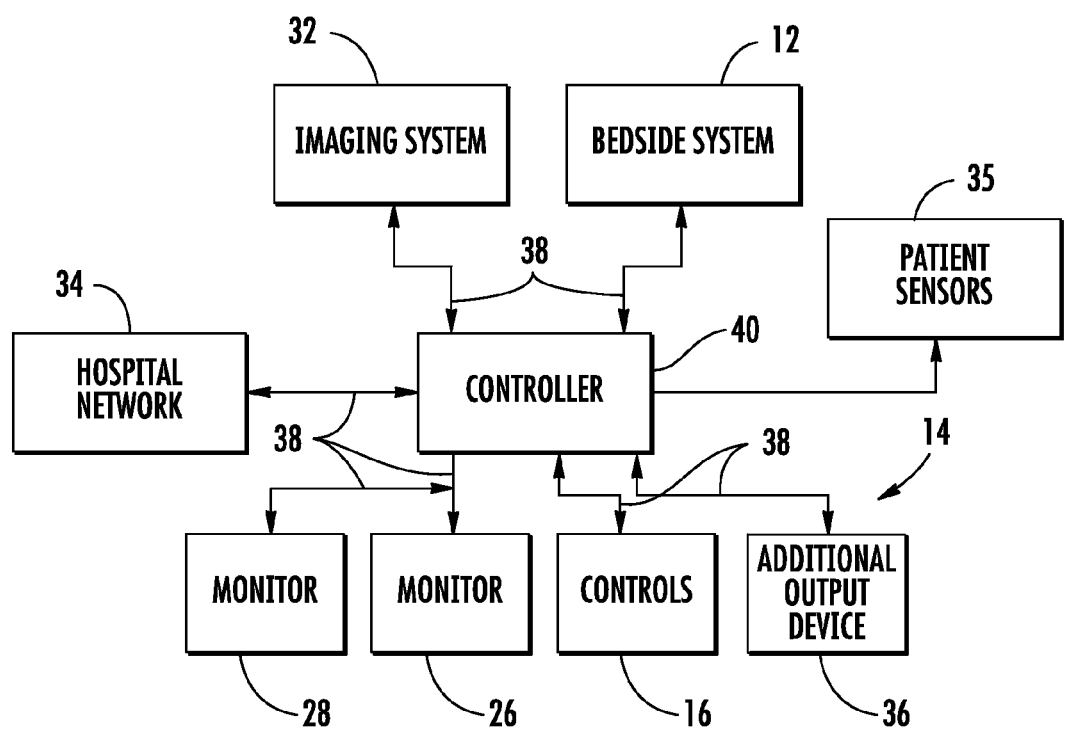
FIG. 2 is block diagram of a robotic catheter system according to an exemplary embodiment.

Referring to FIG. 2, a block diagram of catheter procedure system 10 is shown according to an exemplary embodiment. Catheter procedure system 10 may include a control system, shown as controller 40. As shown in FIG. 2, controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34 and one or more additional output devices 36 (e.g., printer, disk drive, cd/dvd writer, etc.). Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc.

Figure 3:
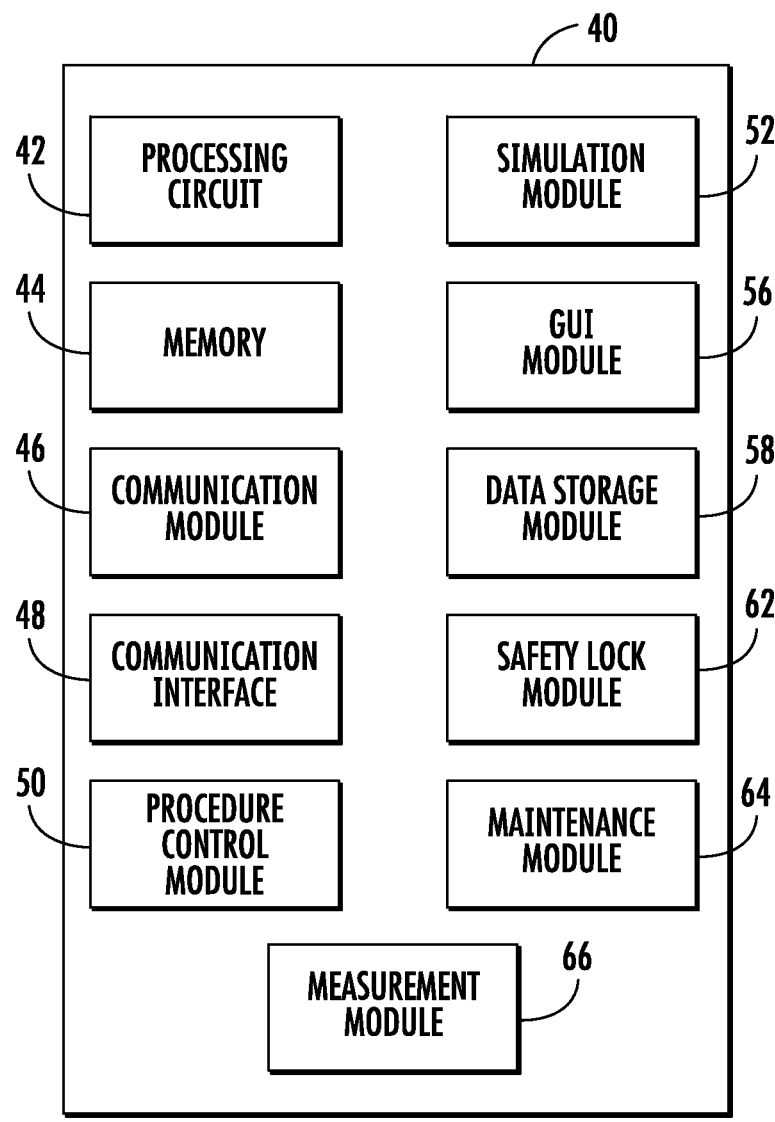
FIG. 3 is a block diagram of a control system according to an exemplary embodiment.

Referring to FIG. 3, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 42, memory 44, communication module or subsystem 46, communication interface 48, procedure control module or subsystem 50, simulation module or subsystem 52, GUI module or subsystem 56, data storage module or subsystem 58, safety lock module or subsystem 62, maintenance module or subsystem 64, and measurement module 66.

Processing circuit 42 may be a general purpose processor, an application specific processor (ASIC), a circuit containing one or more processing components, a group of distributed processing components, a group of distributed computers configured for processing, etc. configured provide the functionality of module components 46, 50-66. Memory 44 (e.g., memory unit, memory device, storage device, etc.) may be one or more devices for storing data and/or computer code for completing and/or facilitating the various processes described in the present disclosure. Memory 44 may include volatile memory and/or non-volatile memory. Memory 44 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 44 is communicably connected to processing circuit 42 (e.g., via a circuit or any other wired, wireless, or network connection) and includes computer code for executing one or more processes described herein. A single memory unit may include a variety of individual memory devices, chips, disks, and/or other storage structures or systems.

Module or subsystems 46, 50-66 may be computer code (e.g., object code, program code, compiled code, script code, executable code, or any combination thereof) for conducting each module's respective functions. Module components 46, 50-66 may be stored in memory 44, or in one or more local, distributed, and/or remote memory units configured to be in communication with processing circuit 42 or another suitable processing system.

Communication interface 48 includes one or more component for communicably coupling controller 40 to the other components of catheter procedure system 10 via communication links 38. Communication interface 48 may include one or more jacks or other hardware for physically coupling communication links 38 to controller 40, an analog to digital converter, a digital to analog converter, signal processing circuitry, and/or other suitable components. Communication interface 48 may include hardware configured to connect controller 40 with the other components of catheter procedure system 10 via wireless connections. Communication module 46 is configured to support the communication activities of controller 40 (e.g., negotiating connections, communication via standard or proprietary protocols, etc.). In one embodiment, communication module 46 may also be configured to support communication between lab unit speaker 13, lab unit microphone 15, workstation speaker 17, and workstation microphone 19. In another embodiment, communication interface 48 may be configured to communicably couple controller 40 to multiple bedside systems and/or multiple imaging systems located in multiple lab units. In this embodiment, communication module 46 may also be configured to allow workstation 14 to control multiple lab units.

Data storage module 58 is configured to support the storage and retrieval of information by controller 40. In one embodiment, data storage module 58 is a database for storing patient specific data, including image data. In another embodiment, data storage module 58 may be located on hospital network 34. Data storage module 58 and/or communication module 46 may also be configured to import and/or export patient specific data from hospital network 34 for use by controller 40.

Controller 40 also includes a procedure control module 50 configured to support the control of bedside system 12 during a catheter based medical procedure. Procedure control module 50 allows the manipulation of controls 16 by the user to operate bedside system 12. Procedure control module 50 may also cause data appropriate for a particular procedure to be displayed on monitors 26 and 28. Procedure control module 50 may include sets of instructions specific to various types of catheter based procedures that may be performed using bedside system 12. For example, procedure control module 50 may include one set of instructions that will be executed by processing circuit 42 if bedside system 12 is being used to perform a diagnostic catheterization procedure and another set of instructions that will be executed by processing circuit 42 if bedside system 12 is being used to perform an therapeutic catheter procedure. In addition, procedure control module 50 may also be configured to allow a user located at workstation 14 to operate imaging system 32. In the exemplary embodiment shown in FIG. 6, procedure control module 50 located at workstation 14 may be configured to control multiple bedside systems, control balloon and/or stent inflation, control contrast media and/or medicine injection, and control multiple imaging systems located in multiple lab units 11.

Figure 7:
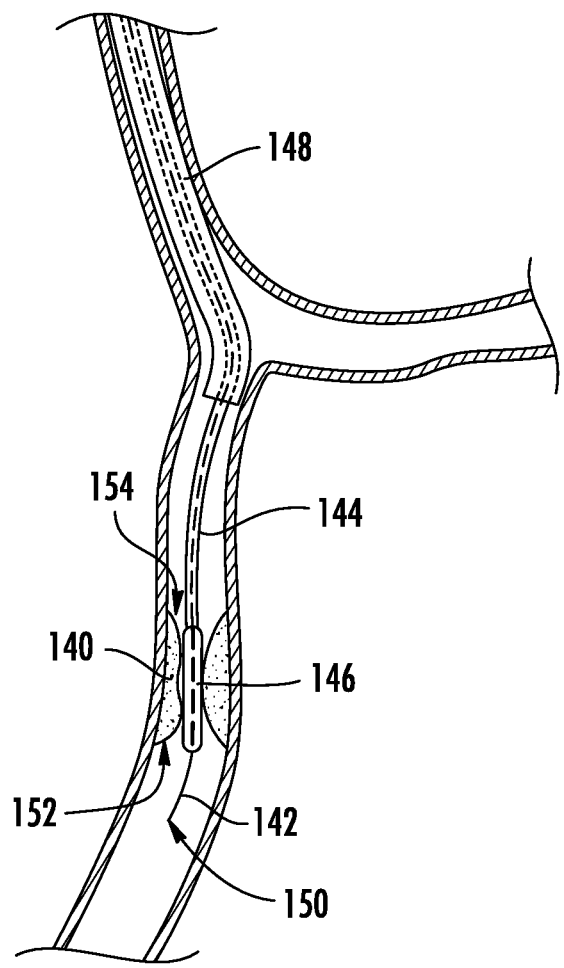
FIG. 7 is an image of coronary arteries shown during a real catheter based therapeutic procedure according to an exemplary embodiment.

Referring to FIG. 7, an exemplary catheterization procedure is shown. During the exemplary balloon angioplasty therapeutic procedure of FIG. 7, an incision is made, usually in the groin. A guide catheter 148 is inserted through the incision into the femoral artery. Bedside system 12 is operated to feed guide catheter 148 through the patient's arterial system until guide catheter 148 is positioned near either the left or right ostium. Bedside system 12 is then operated to feed guide wire 142 through guide catheter 148 until guide wire 142 extends across lesion 140. Next, bedside system 12 is operated to advance working catheter 144 over guide wire 142 to position balloon 146 across lesion 140. Once working catheter 144 and balloon 146 is in place, balloon 146 is inflated to compress lesion 140 and to stretch the artery open thereby increasing blood flow to the heart. Balloon 146 is then deflated, guide wire 142 and working catheter 144 are removed, and the incision is closed.

While the catheter based therapeutic procedure discussed above relates to a balloon angioplasty, it should be understood that the catheter used during a catheterization procedure may be any type of catheter useful during the performance of any percutaneous procedure. For example, the catheter may include a stent that is expanded and left at the site of the lesion. Alternatively, the catheter may include structures adapted to cut or grind away the plaque forming the lesion.

Controller 40 also includes simulation module 52. Simulation module 52 is configured to run a simulated catheterization procedure based upon stored patient specific data (e.g., image data representing a patient's heart) and also based upon a user's manipulation of controls 16. Generally, simulation module 52 is configured to allow a user to manipulate controls 16 during the simulated procedure, to determine how bedside system 12 would respond to the manipulation of these controls if the procedure were not simulated, and, based upon this, to provide feedback to the user regarding the user's performance during the simulated procedure. In one embodiment, simulation module 52 may display an image of a heart on monitor 26 or 28 and display an image of a virtual catheterization component on top of the displayed image. The image of the virtual catheterization component moves relative to the displayed image in response to manipulation of controls 16. In one embodiment various information from or portions of the simulated procedure is recorded.

Controller 40 also includes graphical user interface ("GUI") module 56. GUI module 56 is configured to support the display of information on monitors 26 and 28 and/or on touch screen 18. In one embodiment, during a catheterization procedure, GUI module 56 is configured to display x-ray images of a patient's heart generated by imaging system 32 on first monitor 26, to display hemodynamic data on second monitor 28, and to display graphical user interface ("GUI") 160 on touch screen 18. In another embodiment, GUI module 56 is configured to display images captured during a previous catheter based medical procedure. In one embodiment, the image data is downloaded in advance into data storage subsystem in advance of the next procedure to be performed. GUI module 56 may include a two dimensional graphics engine, a three dimensional graphics engine, and/or any other suitable logic or programming code for generating a GUI having the features described in the present application.

Figure 5:
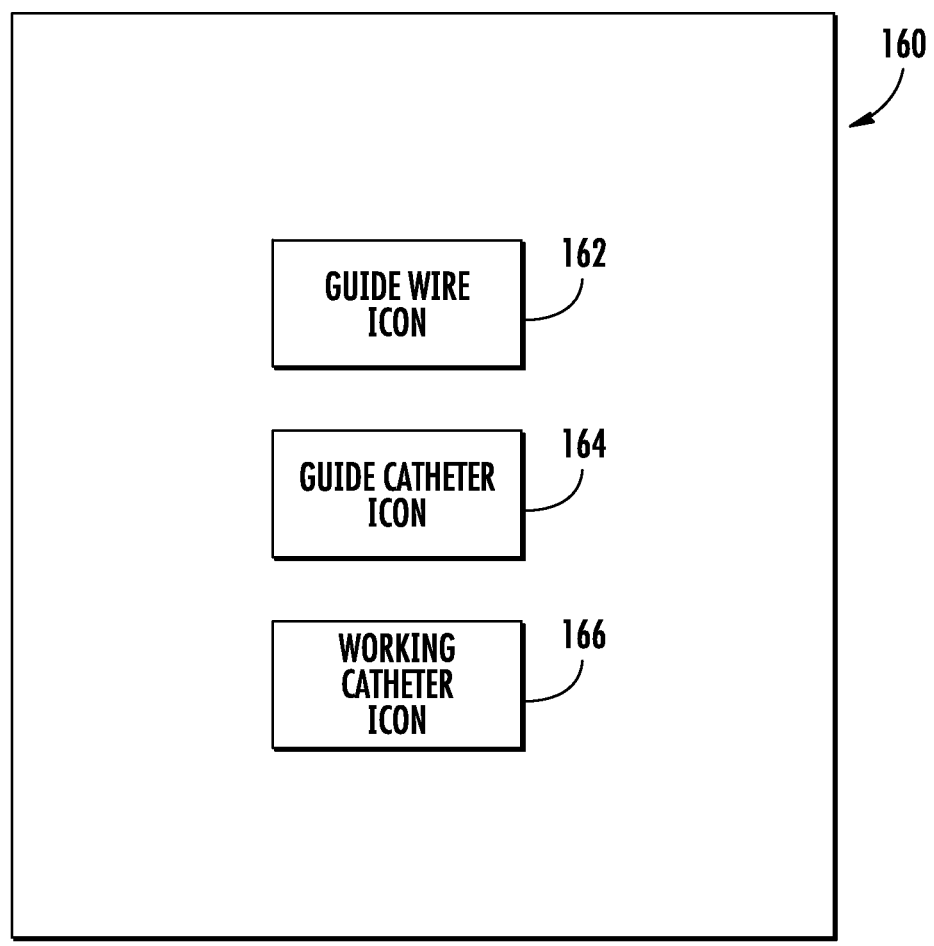
FIG. 5 is a diagram of a graphical user interface according to an exemplary embodiment.

Referring to FIG. 5, in one embodiment GUI module 56 is configured to generate a GUI 160 having an icon representing the operational status of each of the percutaneous intervention devices or components that may be used with bedside system 12. GUI 160 includes a guide wire icon 162, a guide catheter icon 164, and a working catheter icon 166. In one embodiment, GUI module 56 is configured to display icons 162-166 in a manner that illustrates which component bedside system 12 is currently controlling.

In one embodiment, GUI module 56 may be configured to alter the display of guide wire icon 162 when the user is controlling guide wire 142, to alter the display of guide catheter icon 164 when the user is controlling guide catheter 148, and to alter the display of working catheter icon 166 when the user is controlling working catheter 144. In one embodiment, GUI module 56 is configured to color code the icons of GUI 160 based upon whether the corresponding component is currently in use. For example, if controls 16 are currently controlling guide wire 142, guide wire icon 162 may be colored green to indicate that the user is currently controlling the guide wire. In addition, when controls 16 are currently controlling guide wire 142, guide catheter icon 164 and working catheter icon 166 may be colored yellow or grey to indicate that the user is not currently controlling guide catheter 148 or working catheter 144. In other embodiments, GUI module 56 may change the size, change the shape, change the type of graphic, create movement, etc. of the icons of GUI 160 to clearly indicate which component is in currently in use. In one embodiment, GUI module 56 is configured to display icons 162-166 as a moving graphic of the component currently in use. In this embodiment, the movement of the graphic may match the movement experienced by the component. For example, guide wire icon 162 may be an advancing, retracting, or rotating graphic of a guide wire when guide wire 142, is being advanced, retracted, or rotated.

In another embodiment, GUI module 56 is configured to color code icons 162-166 based upon whether the corresponding component has been rendered inoperative by safety lock module 62. For example, if the controls for guide wire 142 have been locked, GUI module 56 may be configured to color guide wire icon 162 red. In addition, GUI module 56 may be configured to color code the image of a particular component shown in the x-ray image of the patient's heart to correspond to the color of the corresponding icon. For example, if guide wire icon 162 is colored green indicating that guide wire 142 is in use, the image of guide wire 142 shown in the x-ray image may also be colored green.

In another embodiment, GUI module 56 may be configured to display icons 162-166 in a manner that clearly indicates which controls are configured to operate which component of beside system 12. In the exemplary embodiment of FIG. 4, GUI module 56 is configured to display icons 162-166 on touch screen 18 such that each icon is positioned above the corresponding control. In one embodiment, the user may assign each of the joysticks shown in FIG. 4 to control a particular component by positioning icons 162-166 over the joysticks. For example, if a user wanted the left most joystick to control the working catheter, the user would touch working catheter icon 166 on touch screen 18 and drag working catheter icon 166 to the portion of touch screen 18 above the left most joystick. In another exemplary embodiment, if guide wire control 23 has a particular shape and/or color, GUI module 56 may be configured to display guide wire icon 162 to have the same shape and/or color as guide wire control 23. In another embodiment, GUI module 56 is configured to display GUI 160 during a simulated catheterization procedure is performed using catheter procedure system 10.

In another embodiment, GUI module 56 may be configured to allow the user to alter the display of image data by interacting with touch screen 18. In one embodiment, GUI 160 may be displayed on touch screen 18 and GUI 160 may include an icon representing the patient's heart. By touching portions of the icon representing the patient's heart, the user may alter the display of real-time images during the performance of a real catheterization procedure or may alter the display of a stored image during the performance of a simulation procedure. For example the user may touch to coronary artery portion of the heart icon to cause the display of the real-time images of the patient's heart to zoom in on (e.g., magnify, increase the screen resolution, etc.) the coronary arteries displayed in the real-time image.

In another embodiment, GUI module 56 is configured to display GUI 160 including icons that represent various information about the procedure currently being preformed. In one embodiment, GUI module 56 displays an icon that shows the distance moved by the various percutaneous intervention devices during the procedure. This distance information may be obtained from encoders in bedside system 12, from the real-time image data, and/or from one or more positional sensors located on the percutaneous intervention devices. In another embodiment, GUI module 56 may display an icon that shows a force that is acting on the percutaneous intervention devices. This force may be generated by bedside system 12 or by a source within the patient (e.g., contraction of the heart, etc.).

In another embodiment, GUI module 56 is configured to display an icon showing the amount of contrast media that has been delivered to the patient during the procedure. In one embodiment, this icon may also indicate the maximum amount of contrast agent that can safely be delivered to the patient. This icon may also indicate the amount of contrast agent that still may be delivered to the patient during the procedure. In one embodiment, this icon may be a meter that has a bar that increases as the amount of contrast media delivered increases. In another embodiment, GUI module 56 is configured to display an icon showing the amount of radiation that has been delivered to a patient during a particular procedure. This icon may also show the maximum amount of radiation that may be delivered during the procedure and may also show the current amount of radiation delivered as a percentage of the total that may be delivered.

In another embodiment, GUI module 56 is configured to display an icon providing information regarding the state of contraction of the heart. Providing this information to the user may allow the user to time operation of various percutaneous intervention devices to a particular stage of the heart beat. For example, the user may want to inject contrast media into the coronary arteries during diastole to prevent dilution of the contrast media that may occur when the heart contracts moving blood through the coronary arteries. In one embodiment, GUI module 56 displays an icon indicating when contrast media should be introduced. In another embodiment, controller 40 automatically injects contrast agent during the appropriate state of contraction of the heart. As another example, the user may time movement of the guide wire so that the guide wire is moved during diastole because the amount of contact (and consequently the resulting frictional force) between the guide wire and the interior wall of the blood vessel tends to be lower during diastole. In one embodiment, GUI module 56 displays an icon of a beating heart that matches the beating of the patient's heart. In another embodiment, GUI module 56 displays an electrocardiogram graph.

In other embodiments, GUI module 56 is configured to display icons indicating various physiological data of the patient. In one embodiment, GUI module 56 displays one or more icons indicating the patient's heart rate, respiratory rate, blood pressure, body temperature, etc. In another embodiment, GUI module 56 may be configured to display icons to indicate that the patient is experiencing a medical problem. For example, GUI module 56 may be configured to display an icon indicating that patient 21 is experiencing cardiac arrest or a seizure, that the patient's breathing has stopped, etc. Display of icons indicating a problem with the patient may be based upon the various measurements taken by patient sensors 35 (e.g., heart rate, blood pressure, etc.) during the catheterization procedure or based upon an automated analysis of the real time images of the patient's heart taken during the procedure.

In other embodiments, GUI module 56 is configured to display GUI 160 including icons that represent various aspects of catheter procedure system 10. In one embodiment, GUI module 56 is configured display a graphical display of the motors, actuators, encoders, etc. that are currently in use or in motion within bedside system 12. In one embodiment, GUI module 56 is configured to display one or more icons (e.g., on/off icons, mute icon, volume icon, etc.) to allow the user located at workstation 14 to control various aspects of the communication system. In another embodiment, GUI module 56 is configured to a display a graphic that indicates that patient 21 located within lab unit 11 is trying to communicate using lab unit mic 15.

In another embodiment, GUI module 56 may be configured to display an icon indicating various information regarding a particular component that is being used with bedside system 12. For example, if a guide wire of a certain size made by a certain manufacturer is being used with bedside system 12, the icon displayed by GUI module 56 will indicate the size and manufacturer of the guide wire. In one embodiment, specific percutaneous intervention devices may include radio frequency identification tags (RFID tags) that include information which identifies the particular component, and catheter procedure system 10 may include an RFID reader to read the RFID tags. In this embodiment, the icon identifying the component displayed by GUI module 56 is based upon the information read from the RFID tag associated with the component.

In another embodiment, GUI module 56 will display a menu listing all of the specific percutaneous intervention devices that may be used with bedside system 12. The user then may select from the menu which component will be used with bedside system 12. Various modules of controller 40 may utilize information about specific percutaneous intervention devices to provide the functionalities of the modules. For example, procedure module 50 may utilize this information to ensure that proper display of information during a catheterization procedure.

In another embodiment, GUI module 56 is configured to display an icon that represents the angioplasty balloon and/or stent that the working catheter is equipped with. In one embodiment, GUI module 56 is configured to display a graphical representation of the balloon and/or stent that expands as the real balloon or catheter expands allowing the user to conveniently see the current state of expansion. In another embodiment, GUI module may be configured to display a bar graph indicating the percentage of the balloon or stent expansion.

In another embodiment, GUI module 56 is configured to display icons representing various information based upon interaction with bedside system 12. In one embodiment, if a physician, nurse, technician, etc. working within lab unit 11 performs an action indicating that a new patient will be operated on in lab unit 11, GUI module 56 may display an icon prompting the user at workstation 14 to load or access the records and/or patient history of the next patient to undergo a procedure within lab unit 11. One event that may trigger the display of this icon is the loading of new percutaneous intervention devices (e.g., a new cassette, etc.) into bedside system 12. In one embodiment, controller 40 may record a summary or produce a summary report of every display generated by GUI module 56 during a catheter based procedure. In one embodiment, the summary report includes all of the details of a catheter based medical procedure (e.g., time, movement of devices, types of devices used, etc.).

Controller 40 also includes a safety lock module 62. Safety lock module 62 is configured to lock, render inoperative, inactivate, etc., one or more portions of controls 16 when the component of bedside system 12 (e.g., guide wires, catheters, catheter balloons, stents, contrast media, medicine, etc.) that corresponds to the inactive portion of control 16 is not currently in use. This may prevent accidental or inadvertent operation of the inactive control or controls. For example, in the embodiment shown in FIG. 4, when the operator is moving a guide wire via operation of guide wire control 23, working catheter control 25 and guide catheter control 29 may be rendered inoperative such that if the user accidentally operates (e.g., inadvertently touches, bumps, etc.) either control, there will be no corresponding movement of the working catheter or the guide catheter. Controls 16 may include a switch, toggle or other means that is configured to allow the user to switch various controls between active and inactive states (e.g., controls 210 and 220 discussed below).

In one embodiment, safety lock module 62 inactivates one or more of the controls by preventing the inactive control from generating a control signal (e.g., the inactive control may be disconnected from a power source). In another embodiment, safety lock module 62 inactivates one or more of the controls by preventing the transmission of a control signal from the inactive control. This may be accomplished by introducing a reversible break in one of the communication links 38 that connect the inactive control to bedside system 12. In another embodiment, safety lock module 62 inactivates one or more of the controls by causing bedside system 12 or one of the intermediate subsystems of controller 40 (e.g., procedure control module 50) to ignore the control signal generated by the inactive control.

Controller 40 also includes maintenance module 64. Maintenance module 64 is configured to allow a technician to perform various maintenance tasks on catheter procedure system 10. Maintenance module 64 may allow a technician to calibrate various components of catheter procedure system 10 (e.g., motors within bedside system 12, controls 16, etc.). Maintenance module 64 may also be configured to allow the technician to reinstall, update, upgrade, etc. any of the software components of catheter procedure system 10. Maintenance module 64 may also be configured to allow the technician to perform diagnostic tests to aid in the isolation and repair of a malfunction. In one embodiment, maintenance module 64 is configured to allow the technician to switch between a maintenance mode, and/or procedure mode.

Controller 40 also includes measurement module 66. Measurement module 66 is configured to measure the length of a structure utilizing catheter procedure system 10 by measuring the distanced moved by a percutaneous device as the percutaneous device traverses the length of the structure. In this embodiment, catheter procedure system 10 includes one or more devices or components for measuring the distance moved by the percutaneous device (e.g., guide wire 142). For example, bedside system 12 may be equipped with one or more encoders that measure movement of rollers that impart movement to the guide wire. In other embodiments, however, other measurement devices for determining the amount of guide wire movement may be used.

Figure 8:
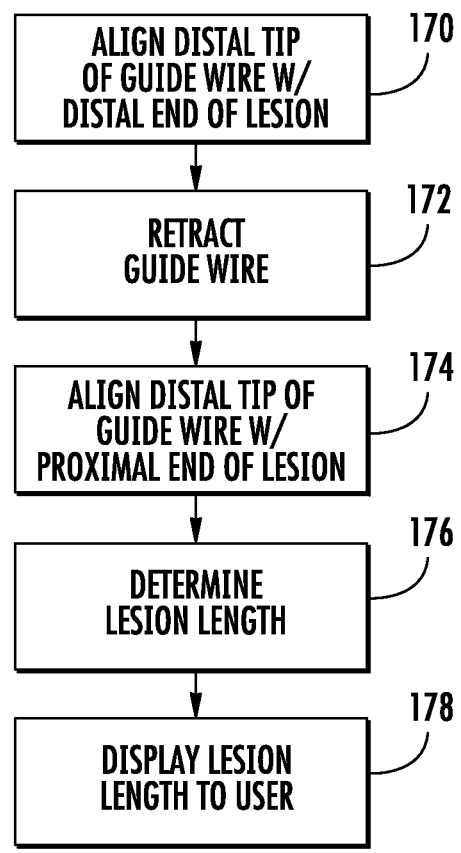
FIG. 8 is a flow diagram showing measurement of a length according to an exemplary embodiment.

Referring to FIGS. 7 and 8, an exemplary embodiment of measurement module 66 is described for measuring the length of a vascular lesion. As shown in FIG. 7, lesion 140 includes a distal end 152 and a proximal end 154, and guide wire 142 includes a distal tip 150. Referring to FIG. 8, to measure the length of lesion 140, at step 170 the user operates controls 16 to cause bedside system 12 to move guide wire 142 so that distal tip 150 of guide wire 142 is aligned with distal end 152 of lesion 140. The user then activates measurement module 66 by, for example, selecting a measurement mode icon displayed on touch screen 18. With measurement module 66 activated, at step 172, the user operates controls 16 to cause guide wire 142 to retract. At step 174, the user continues to operate controls 16 to retract guide wire 142 until distal tip 150 of guide wire 142 is aligned with proximal end 154 of lesion 140. Next the user indicates that distal tip 150 of guide wire 142 is aligned with proximal end 154 of lesion 140 by, for example, selecting a measurement complete icon displayed on touch screen 18. At step 176, measurement module 66 calculates the distance that guide wire 142 was retracted between distal end 152 and proximal end 154 of lesion 140. In one embodiment, the distance that guide wire 142 was retracted is determined from a device, such as an encoder, that measures (directly or indirectly) the distance that guide wire 142 travels as discussed above. The distance that guide wire 142 was retracted is approximately the same length of lesion 140. At step 178, measurement module 66 then causes the display of the lesion length to the user.

The length of the lesion may then be used to select the appropriate size device (e.g., stent, angioplasty balloon, etc.) for treatment of the lesion. In one embodiment, the user performs measurement of the lesion by watching the positioning of the guide wire relative to the lesion on the live, real-time angiographic images of the patient displayed on monitor 26 and/or 28. In another embodiment, lesion length may be measured by measuring the length of the 2D angiographic image of the lesion. However, because the 2D image of the lesion may distort the 3-dimensional length of the lesion, indirect measurement of lesion length by measuring guide wire movement, as discussed above, often results in a more accurate measurement of lesion length than measurement from a 2D image.

In various embodiments, distal tip 150 of guide wire 142 is configured to facilitate location by the user. In one embodiment, distal tip 150 may be configured to be easily seen on an x-ray based image of the patient. For example, distal tip 150 of guide wire 142 may be made more radio-opaque than the rest of guide wire 142. In another embodiment, distal tip 150 of guide wire 142 emits radiation that is detected by imaging system 32.

In various embodiments, measurement module 66 may be integrated with other devices or systems to provide additional and/or different measurements of various lesion characteristics. For example, measurement module 66 may be configured to utilize an intravascular ultrasound (IVUS) catheter system and/or an optical coherence tomography (OCT) system to measure various characteristics of a lesion and to cause a display of information related to the measured characteristic on one or more of the display devices of workstation 14. In addition to lesion length, measurement module 66 may be configured to utilize one or more measurement systems to measure and display information related to characteristics of a lesion in addition to lesion length (e.g., amount of vascular occlusion, degree of calcification, etc.).

Figure 9:
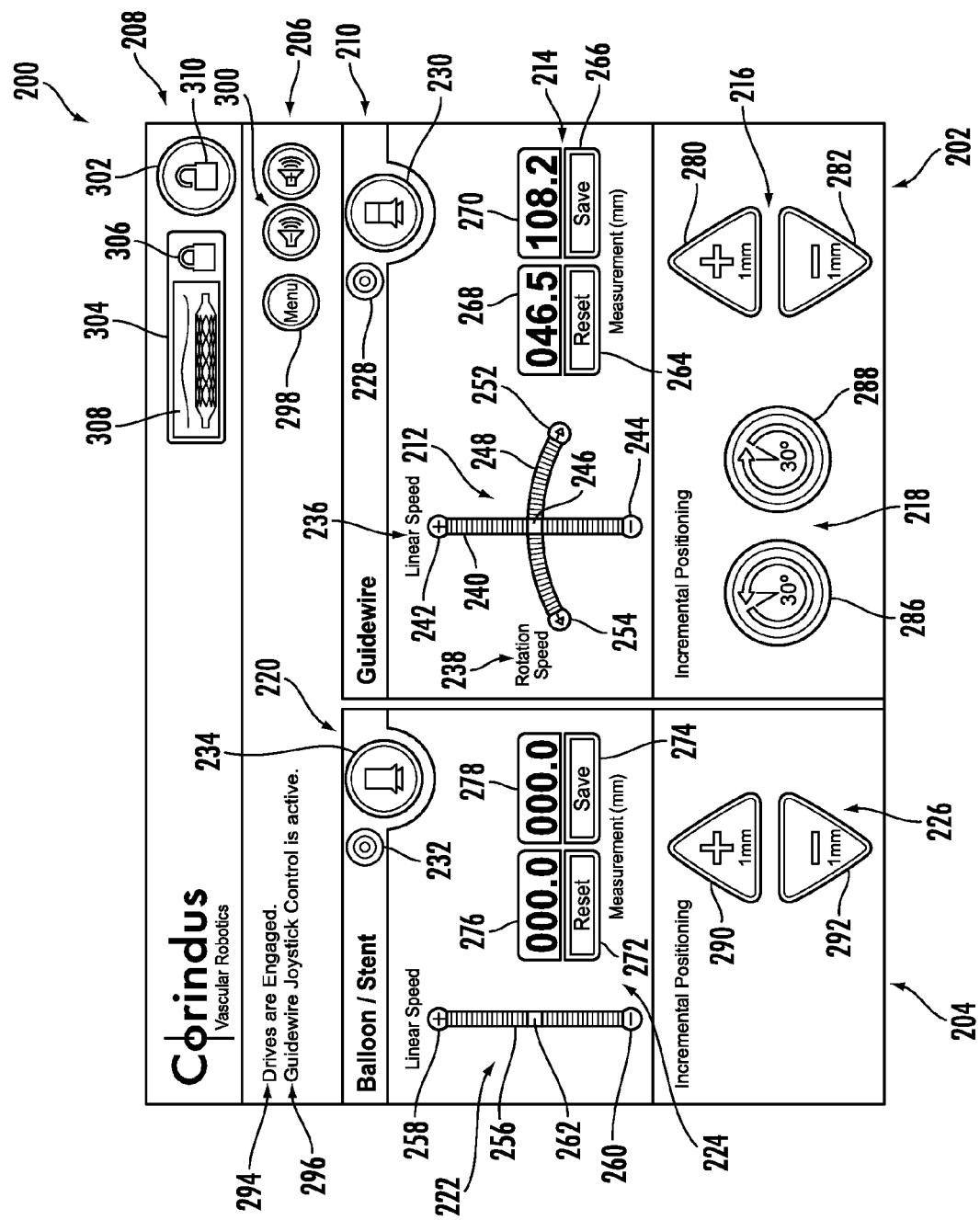
FIG. 9 is a graphical user interface according to an exemplary embodiment.

Referring to FIG. 9, in one exemplary embodiment, GUI module 56 may be configured to cause the display of a graphical user interface (GUI) 200. In the embodiment shown, GUI 200 includes a guide wire panel 202, a working catheter panel, shown as balloon/stent panel 204, system panel 206, and a device engagement panel 208. In the embodiment shown, GUI 200 is displayed on touch screen 18 allowing the user to interact with the various icons by touching the touch screen generating inputs to be processed by the appropriate modules or subsystems of controller 40. In other embodiments, GUI 200 may be displayed on a non-touch screen display with the user interacting with the icons via one or more input device (e.g., mouse, keyboard, etc.). In the embodiment shown, GUI 200, in combination with the other control elements of control 16 (e.g., guide wire control 23, working catheter control 25, etc.), allows a user to control bedside system 12 to move a guide wire and/or a working catheter equipped with a balloon and/or stent to perform a procedure. It should be understood that, while the embodiment of GUI 200 shown relates primarily to the control of a guide wire and a working catheter equipped with a balloon and/or stent, GUI 200 may be modified for the display and control of any device (e.g., guide catheter, imaging catheter, etc.) that may be operated via workstation 14.

In the embodiment shown, guide wire panel 202 includes various GUI elements related to the control and position of the guide wire. Guide wire panel 202 includes an activation control 210, a guide wire speed indicator 212, a guide wire measurement control 214, a guide wire axial step control 216, and a guide wire rotational step control 218. Balloon/stent panel 204 includes various GUI elements related to the control and position of the balloon and/or stent. Balloon/stent panel 204 includes an activation control 220, balloon/stent speed indicator 222, a balloon/stent measurement control 224, and a balloon/stent axial step control 226.

In the embodiment of FIG. 9, controls 210 and 220 allow the user to implement the functionality of safety lock module 62 discussed above. Guide wire activation control 210 allows a user to toggle the guide wire related controls between active and inactive states. Activation control 210 includes a status icon 228 and a toggle button 230 which is pressed by the user to toggle between the active and inactive states. In the embodiment shown, button 230 includes an icon representative of the guide wire control 23 (a joystick in the embodiment shown). When control 210 is toggled to the inactive state, the guide wire control elements (e.g., control 23, controls of guide wire panel 202) are disabled such that if a user interacts with one of the control elements there will be no corresponding movement of the guide wire caused by bedside system 12. When the guide wire controls are inactive, status icon 228 and button 230 are displayed in a first color (e.g., grey, red, etc.) to indicate to the user that the guide wire control elements are inactive. When control 210 is toggled to the active state, the guide wire control elements (e.g., control 23, controls of guide wire panel 202) are enabled such that if a user manipulates one of the control elements bedside system 12 will cause the guide wire to move based on the manipulation of the control. When the guide wire controls are active, status icon 228 and button 230 are displayed in a second color (e.g., green, blue, etc.) to indicate to the user that the guide wire control elements are active.

Balloon/stent activation control 220 allows a user to toggle the working catheter related controls between active and inactive states. Activation control 220 includes a status icon 232 and a toggle button 234 which is pressed by the user to toggle between the active and inactive states. In the embodiment shown, button 234 includes an icon representative of working catheter control 25 (a joystick in the embodiment shown). When control 220 is toggled to the inactive state, the working catheter control elements (e.g., control 25, controls of balloon/stent panel 204) are disabled such that if a user interacts with one of the control elements there will be no corresponding movement of the working catheter caused by bedside system 12. When the working catheter controls are inactive, status icon 232 and button 234 are displayed in a first color (e.g., grey, red, etc.) to indicate to the user that the working catheter control elements are inactive. When control 220 is toggled to the active state, the working catheter control elements (e.g., control 25, controls of balloon/stent panel 204) are enabled such that if a user manipulates one of the control elements bedside system 12 will cause the working catheter (and any balloon/stent that the working catheter is equipped with) to move based on the manipulation of the control. When the working catheter controls are active, status icon 232 and button 234 are displayed in a second color (e.g., green, blue, etc.) to indicate to the user that the working catheter control elements are active.

In use the user may toggle the currently active set of controls to the inactive state before toggling the other set of controls to the active state. However, in one embodiment, safety lock module 62 may be configured to allow both the guide wire controls and the working catheter controls to be active at the same time if both control 210 and 220 are toggled to the active state by the user. In another embodiment, safety lock module 62 may be configured to prevent both the guide wire controls and the working catheter controls to be active at the same time requiring the user to inactivate one set of controls before activating the other set of controls. In one embodiment, when the controls for the device are inactivated, safety lock module 62 is configured to cause bedside system 12 to hold the position of the device fixed until the controls for the device are reactivated (i.e., the device does not move relative to the drive mechanisms of bedside system 12 and/or relative to the patient). For example, the drive mechanisms of bedside system 12 may be configured to engage the inactive device with enough force to prevent unwanted movement of the device relative to the bedside system and/or to the patient.

Guide wire speed indicator 212 provides information to the user regarding the current movement of the guide wire. As shown, guide wire speed indicator 212 includes a linear or axial speed indicator 236 to display information related to the linear speed of the guide wire and a rotational speed indicator 238 to display information related to the rotational speed of the guide wire. Linear speed indicator 236 includes a vertically displayed bar 240 extending between a maximum forward icon 242 indicating the maximum forward speed, a maximum reverse icon 244 indicating the maximum reverse speed of the guide wire, and an origin 246 indicating zero linear movement. As the user manipulates the guide wire controls to advance or retract the guide wire, bar 240 between origin 246 and either icon 242 or icon 244 changes color in proportion to the speed of the guide wire. For example, if the guide wire is currently being advanced at half of the maximum speed, the first half of vertical bar 240 extending above origin 246 changes color.

Rotational speed indicator 238 includes a curved horizontally displayed bar 248 extending between a left (i.e., counterclockwise) rotation icon 250 indicating the maximum left rotational speed and a right (i.e., clockwise) rotation icon 252 indicating the maximum right rotational speed. As the user manipulates the guide wire controls to rotate the guide wire, bar 248 between origin 246 and either icon 250 or icon 252 changes color in proportion to the rotational speed of the guide wire. For example, if the guide wire is currently being rotated at half the maximum speed to the right, the first half of horizontal bar 248 extending from origin 246 toward right rotation icon 252 changes color.

Balloon/stent speed indicator 222 provides information to the user regarding the current movement of the balloon/stent that the working catheter is equipped with. In the embodiment shown, indicator 222 provides information related to the linear speed of the working catheter. Indicator 222 includes a vertical bar 256 extending between a maximum forward icon 258 indicating the maximum forward speed, a maximum reverse icon 260 indicating the maximum reverse speed, and an origin 262 indicating zero linear movement. As the user manipulates the working catheter controls to advance or retract the balloon/stent, bar 256 between origin 262 and either icon 258 or icon 260 changes color in proportion to the speed of the balloon/stent. For example, if the balloon/stent is currently being advanced at half of the maximum speed, the first half of vertical bar 256 extending above origin 262 changes color.

Guide wire measurement control 214 includes a reset button 264, a save button 266, distance indicator 268, and a stored distance indicator 270. When pushed, reset button 264 resets the value displayed by distance indicator 268 causing distance indicator 268 to display 000.0. As the guide wire is advanced and retracted, distance indicator 268 displays the net distance that the guide wire has moved since the last time reset button 264 was pushed (in mm in the embodiment shown). In this manner, distance indicator 268 displays the length of the path that the guide wire traveled from the point when the reset button was pushed to its current position. Thus, distance indicator 268 provides information regarding the current position of the guide wire relative to the position when reset button 264 was last pushed. When save button 266 is pushed, the current value displayed in distance indicator 268 is saved and displayed in stored distance indicator 270.

In the embodiment of FIG. 9, the functionality of measurement module 66 is provided via guide wire measurement control 214. To measure the length of a lesion using guide wire measurement control 214, the user will press reset button 264 when the tip of the guide wire is aligned with the distal tip of the lesion. The user will then retract the guide wire until the distal tip of the guide wire is aligned with the proximal tip of the lesion. When aligned, the user will press save button 266. The number displayed in stored distance indicator 270 will be the distance that the guide wire traveled from the distal to proximal ends of the lesion. The distance traveled using this procedure provides a measurement of the length of the lesion.

Balloon/stent measurement control 224 includes a reset button 272, a save button 274, a distance indicator 276, and a stored distance indicator 278. When pushed, reset button 272 resets the value displayed by distance indicator 276 causing distance indicator 276 to display 000.0. As the working catheter is advanced and retracted, distance indicator 276 displays the net distance that the working catheter has moved since the last time reset button 272 was pushed. In this manner, distance indicator 276 displays the length of the path that the working catheter traveled from the point when the reset button was pushed to its current position (in mm in the embodiment shown). When save button 274 is pushed, the current value displayed in distance indicator 276 is saved and displayed in stored distance indicator 278.

The positional information displayed in distance indicators 268, 270, 276, and/or 278 may be used by the user to help in positioning the guide wire or stent/balloon, respectively. For example, the user may know the distance that the guide wire must travel to reach a particular point within the patient. Thus, for example, the positional information displayed in the various indicators helps the user determine if the device has been moved too far, not far enough etc. In addition, knowing the remaining distance to a particular point may allow a user to plan upcoming movements of the device. For example, the user may begin to rotate the guide wire some distance before a branch in the patient's vascular system so that the guide wire is properly aligned when the tip of the guide wire reaches the branch.

Guide wire panel 202 includes a guide wire axial step control 216 and a guide wire rotational step control 218. Axial step control 216 includes an advance button 280 and a retract button 282 that, when pushed, cause bedside system 12 to advance or retract, respectively, the guide wire by the step distance associated with button 280 and/or 282. In the embodiment shown, the step distance for both button 280 and 282 is 1 mm. Rotational step control 218 includes a left rotation button 286 and a right rotation button 288 that, when pushed, cause bedside system 12 to rotate the guide wire to left or right, respectively, by the angular step associated with button 286 and/or 288. In the embodiment shown, the angular step distance for both button 286 and 288 is 30 degrees. In other embodiments, other step distances are associated with the step controls (e.g., 1 mm, 2 mm, 3 mm, etc. axial steps, and 10 degree, 15 degree, 20 degree, 40 degree, etc. rotational steps).

Balloon/stent panel 204 includes a balloon/stent axial step control 226. Balloon/stent axial step control 226 includes an advance button 290 and a retract button 292 that, when pushed, cause bedside system 12 to advance or retract, respectively, the balloon/stent equipped working catheter by the step distance associated with button 290 and/or 292. In the embodiment shown, the step distance for both button 290 and 292 is 1 mm. In other embodiments, the steps associated with the various buttons need not be the same. For example, the retract step may be 2 mm and the advance step may be 1 mm.

System panel 206 includes a bedside system status indicator 294, a control indicator 296, a menu button 298, and volume buttons 300. Bedside system status indicator 294 displays information related to the current operating status of bedside system 12. In the embodiment shown, indicator 294 indicates that the drive elements of bedside system 12 that impart movement to the guide wire and working catheter are engaged. Indicator 294 may indicate other states of bedside system 12 (e.g., disengaged, covers open, no power, various error messages, etc.). Control indicator 296 displays information related which controls are active. As shown, control indicator 296 indicates that the guide wire joystick control (i.e., an embodiment of guide wire control 23) is active. Volume buttons 300 allow the user to increase or decrease the volume of various auditory alerts and signals generated by workstation 14. When pushed, menu button 298 causes a drop down menu with various options to be displayed. In one embodiment, the drop down menu displayed by pushing menu button 298 includes a cancel/return button that closes the drop down menu, a restart application button that restarts the software of workstation 14, an exit/shut down option that powers down controls 16 and/or workstation 14, and an "about software" button that displays information related to the version of the software installed on workstation 14.

GUI 200 includes a device engagement panel 208. Device engagement panel 208 includes an engage/disengage control 302 and a bedside system indicator 304. Engage/disengage control 302, when pushed by the user, causes bedside system 12 to move between a loading position and a use position. If bedside system 12 is currently in the loading position, pressing control 302 will cause bedside system 12 to move to the engaged, use position. If bedside system 12 is currently in the use position, pressing control 302 will cause bedside system to move to the disengaged, loading position. In the loading position, the various drive mechanisms of bedside system 12 are disengaged from the percutaneous devices (e.g., guide wire, working catheter, etc.) of bedside system 12 and the covers are unlocked and opened. In the loading position, new percutaneous devices may be loaded into bedside system 12 and the current percutaneous devices may be removed. In the use position, the various drive mechanisms of bedside system 12 are engaged with the percutaneous devices of bedside system 12 such that bedside system 12 is able to impart movement to the devices and the covers are closed and locked.

In the embodiment shown, engage/disengage control 302 includes a lock icon 310. Lock icon 310 provides an indication to the user regarding whether pushing control 302 will results in engagement or disengagement of bedside system 12 from the percutaneous devices. For example, if lock icon 310 is shown unlocked, as in FIG. 9, pushing control 302 will cause bedside system 12 to move from the engaged, use position to the disengaged, loading position. If lock icon 310 is shown locked (not shown), pushing control 302 will cause bedside system 12 to move from the disengaged, loading position to the engaged, use position.

Bedside system indicator 304 provides information related to the current position (e.g., loading, use) of bedside system 12. For example, indicator 304 indicates whether bedside system 12 is in the disengaged, loading position or the engaged, use position. In one embodiment, indicator 304 is displayed in one color (e.g., green, blue, etc.) if bedside system 12 is in the engaged, use position and in a second color (e.g., yellow, red, etc.) if bedside system 12 is in the disengaged, loading position. In the embodiment shown, indicator 304 may also include a lock icon 306. If lock icon 306 is shown locked, as in FIG. 9, bedside system 12 is currently in the engaged, use position. If lock icon 306 is shown unlocked, bedside system 12 is currently in the disengaged, loading position.

Indicator 304 also includes a percutaneous devices icon 308 that provides an indication of the types of percutaneous devices that bedside system is equipped with. For example, as shown, devices icon 308 indicates that bedside system 12 is equipped with a guide wire and a stent-equipped working catheter. In other embodiments, devices icon 308 may show different and/or more detailed information (e.g., make, model, size, type, etc.) of the devices that bedside system 12 is equipped with.

The exemplary embodiments illustrated in the figures and described herein are offered by way of example only. Accordingly, the present application is not limited to a particular embodiment, but extends to various modifications that nevertheless fall within the scope of the appended claims and also extends to any combination of the features or elements described herein or set forth in the claims.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. All such modifications are intended to be included within the scope of the present disclosure.

The order or sequence of any process or method steps may be varied or re-sequenced according to alternative embodiments. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes, and omissions may be made in the design, operating conditions and arrangement of the exemplary embodiments without departing from the scope of the present disclosure.

What is claimed is:

1. A remote workstation for the control of percutaneous intervention devices comprising:
   a control system configured to remotely and independently control at least two percutaneous intervention devices, the control system including at least one input device to control the percutaneous intervention devices, wherein the control system controls movement of at least one of the percutaneous intervention devices along at least two degrees of freedom;
   a graphical user interface configured to display a first set of icons representative of the operational status of the at least two percutaneous intervention devices, wherein the first set of icons comprises dynamically displayed icons, and to display second set of icons representative of physiological information of a patient, and
   a measurement module configured to allow a user to measure the length of a structure by aligning the tip of one of the percutaneous devices controlled by the control system with the distal end of the structure, withdrawing the tip until it is aligned with the proximate end of the structure and measuring the distance moved by the percutaneous intervention device as the percutaneous intervention device traverses the length of the structure, wherein the measurement module is configured to cause the display of the measured length on a display device.

2. The remote workstation of claim 1 wherein the percutaneous intervention devices include at least two of a catheter guide wire, a working catheter, a guide catheter, a stent, and an angioplasty balloon, and further wherein the at least two degrees of freedom include axial movement and rotation.

3. The remote workstation of claim 1 wherein operational status includes an indication of the current movement speed of the at least two percutaneous intervention devices.

4. The remote workstation of claim 1 wherein the first set of icons are displayed in a first color to indicate that at least one of the percutaneous intervention devices is active and are displayed in a second color to indicate that at least one of the percutaneous intervention devices is inactive.

5. The remote workstation of claim 1 wherein, when at least one of the percutaneous intervention devices is inactive, the control system is configured to hold the at least one inactive percutaneous intervention device such that the at least one percutaneous device is not permitted to move axially relative to a patient on which a procedure is being performed.

6. The remote workstation of claim 1 wherein the first set of icons provide at least one of a visual indication of movement of the at least two percutaneous intervention devices and a visual indication of the physical position of the at least one input device.

7. The remote workstation of claim 1 wherein the graphical user interface displays an additional icon representative of an amount of contrast agent delivered to a patient during a medical procedure.

8. The remote workstation of claim 1 wherein the graphical user interface displays an additional icon that provides information regarding at least one of the type, manufacturer, size, and material of one of the percutaneous intervention devices being controlled.

9. The remote workstation of claim 1 wherein the graphical user interface displays an additional icon representative of the state of contraction of the patient's heart, wherein the additional icon is an animated image of a beating heart that moves to match the state of contraction of the patient's heart.

10. The remote workstation of claim 1 further comprising a touch screen, wherein the graphical user interface displays an additional icon on the touch screen that is a graphical representation of a heart, wherein the additional icon is touched to change a display of a real-time image of the patient's heart.

11. The remote workstation of claim 10 wherein the display of the real-time image of the patient's heart zooms in on a portion of the patient's heart corresponding to a portion of the additional icon that is touched.

* * * * *